United States Patent
Kozlov et al.

(10) Patent No.: US 11,318,291 B2
(45) Date of Patent: May 3, 2022

(54) DEVICE FOR THE CONSERVATIVE TREATMENT OF NASAL AND PARANASAL SINUS DISEASES

(71) Applicants: Stepan Evgenevich Kudryashov, selo Nemchinovka (RU); Irina Ivanovna Kozlova, Moscow (RU)

(72) Inventors: Vladimir Sergeevich Kozlov, Moscow (RU); Stepan Evgenevich Kudryashov, selo Nemchinovka (RU)

( * ) Notice: Subject to any disclaimer, the term of this patent is extended or adjusted under 35 U.S.C. 154(b) by 62 days.

(21) Appl. No.: 16/630,680

(22) PCT Filed: Jun. 22, 2018

(86) PCT No.: PCT/RU2018/000416
§ 371 (c)(1),
(2) Date: Jan. 13, 2020

(87) PCT Pub. No.: WO2019/017817
PCT Pub. Date: Jan. 24, 2019

(65) Prior Publication Data
US 2021/0085940 A1 Mar. 25, 2021

(30) Foreign Application Priority Data
Jul. 21, 2017 (RU) .......................... RU2017126150

(51) Int. Cl.
*A61M 31/00* (2006.01)
*A61B 17/12* (2006.01)
(Continued)

(52) U.S. Cl.
CPC ....... *A61M 31/00* (2013.01); *A61B 17/12104* (2013.01); *A61B 17/12136* (2013.01);
(Continued)

(58) Field of Classification Search
CPC .............. A61B 17/12136; A61B 17/24; A61B 2017/246; A61M 2025/1052;
(Continued)

(56) References Cited

U.S. PATENT DOCUMENTS

| 4,351,330 A | * | 9/1982 | Scarberry | .............. G02B 27/01 |
| | | | | 128/207.15 |
| 2016/0038723 A1 | * | 2/2016 | Tsukada | ............. A61M 25/1011 |
| | | | | 604/101.03 |

* cited by examiner

*Primary Examiner* — Deanna K Hall
(74) *Attorney, Agent, or Firm* — Kreydin

(57) ABSTRACT

The invention relates to medical technology, and more particularly to a device for the conservative treatment of nasal and paranasal sinus diseases. The present device comprises obturators for the posterior and anterior nasal openings, each obturator being in the form of an expandable sheath made of a resilient material and provided with a feed tube. The distal end of the tube is in communication with the cavity below the sheath, and the proximal end is provided with an adapter having a valve mechanism. The obturator sheath for the posterior nasal opening is hermetically fastened to the distal portion of its feed tube. The obturator sheath for the anterior nasal opening is hermetically fastened to a cuff. The cuff is provided with two channels, one of which holds the feed tube of the obturator sheath for the posterior nasal opening in such a way that the cuff can move along the entire length of the feed tube. The other channel holds a catheter for evacuating a pathological secretion from the paranasal sinuses and/or for introducing solutions of medicinal preparations into same for diagnostic or therapeutic purposes. The catheter is held in said channel in such a way that the distal portion thereof can be moved into the space between the obturator sheaths. The invention is intended to provide more effective treatment of nasal and paranasal sinus disorders.

13 Claims, 13 Drawing Sheets

(51) Int. Cl.
*A61M 39/10* (2006.01)
*A61M 25/00* (2006.01)
(52) U.S. Cl.
CPC ... *A61M 39/10* (2013.01); *A61B 2017/12127* (2013.01); *A61M 25/005* (2013.01); *A61M 2039/1077* (2013.01); *A61M 2210/0618* (2013.01); *A61M 2210/0681* (2013.01)
(58) Field of Classification Search
CPC .. A61M 2025/1061; A61M 2039/1077; A61M 2210/0618; A61M 2210/0681; A61M 25/005; A61M 25/0068; A61M 25/1011; A61M 25/1025; A61M 2025/1072; A61M 2025/1054
See application file for complete search history.

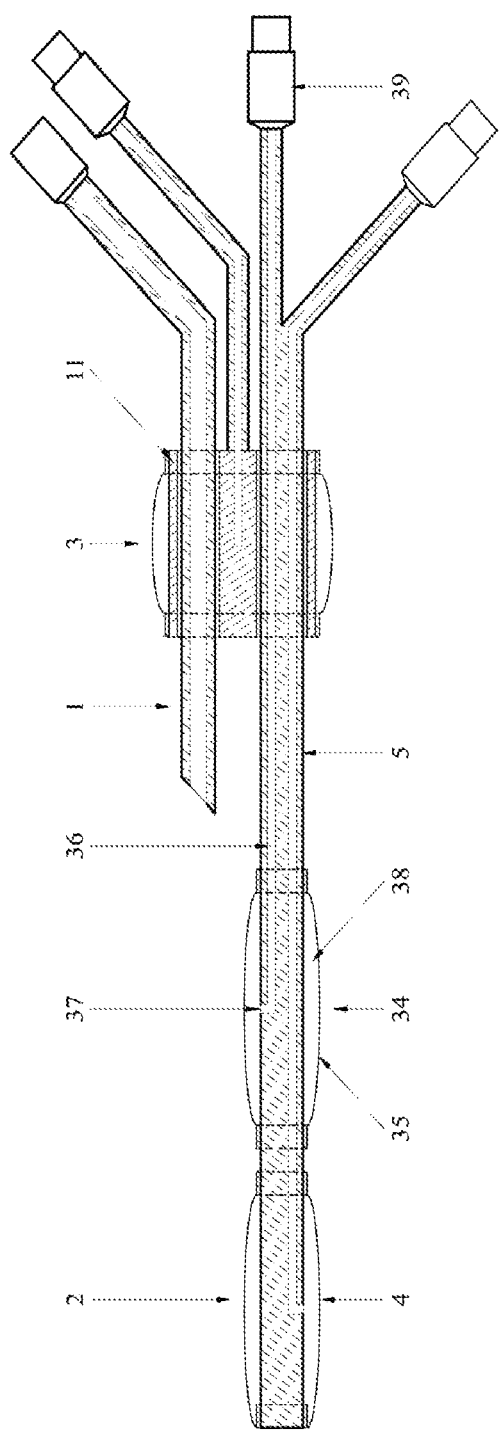

DEVICE FOR THE CONSERVATIVE TREATMENT OF NASAL AND PARANASAL SINUS DISEASES

This invention relates to medicine, more specifically to otorhinolaryngology, and may be used to provide conservative treatment of nose and paranasal sinuses diseases requiring pathological secretion to be evacuated from the paranasal sinuses and/or to administer pharmaceutical solutions into the paranasal sinuses for diagnostic or treatment purposes and to staunch nasal bleeding resulting from a treatment procedure.

One known device for the conservative treatment of nose and paranasal sinuses diseases comprises obturators for the anterior and posterior nasal apertures, each configured as an expandable shell made of elastic material and provided with a feed tube whose distal end is in communication with a cavity under the shell and whose proximal end is provided with an adapter having a valve mechanism; the posterior nose opening obturator shell is tightly fixed at the distal section of its feed tube, and the anterior nose opening obturator shell is tightly fixed onto the sleeve, the sleeve having two channels one of which houses the posterior nose opening obturator feed tube such that the sleeve is movable throughout the feed tube length, and the other channel houses a catheter used to evacuate pathological secretion from the paranasal sinuses and/or to administer pharmaceutical solutions into the paranasal sinuses for diagnostic or treatment purposes (see EP 2977014 published on Jan. 27, 2016). One potential issue with the known invention may be the blocking of the catheter drainage port by the nasal mucosal edema of the inferior turbinate caused by inflammation, thus making it difficult to properly evacuate pathological secretion from the paranasal sinuses and to evenly distribute a pharmaceutical solution in the sinuses which greatly diminishes the efficacy of the procedure. Said factors are attributed to the fact that a catheter cannot be inserted deep enough to reach the middle and superior nasal meatuses, i.e. directly to the area of the natural ostia of the paranasal sinuses which enables a catheter to function as appropriate. Furthermore, nasal bleeding out of the blood vessels providing blood supply of the nasal mucosa may be caused in the nasal cavity by intermittent pressure during a treatment procedure. The known invention does not allow such bleeding to be staunched.

The closest analog of the proposed device is a device designed for the conservative treatment of nose and paranasal sinuses diseases, comprising anterior and the posterior nose opening obturators, each of which is configured as an expandable shell made of elastic material and provided with a feed tube whose distal end is in communication with a cavity under the shell and whose proximal end is provided with an adapter having a valve mechanism, the posterior nose opening obturator shell being tightly fixed at the distal section of its feed tube, and the anterior nose opening obturator shell is tightly fixed onto the sleeve, the sleeve having two channels one of which houses the posterior nose opening obturator feed tube such that the sleeve is movable throughout the feed tube length, and the other channel houses a catheter used to evacuate pathological secretion from the paranasal sinuses and/or to administer pharmaceutical solutions into the paranasal sinuses for diagnostic or treatment purposes (see USSR Invention Certificate No. 1768141 published on Oct. 15, 1992). This device has disadvantages similar to those attributed to the invention described above.

The proposed technical solution is aimed at addressing the issue and to achieve the technical result of improving the efficiency of treatment of nose and paranasal sinuses diseases by bringing a catheter close to the nasal cavity to enable the catheter to function as appropriate, to upgrade its operational properties and to add functions facilitating high treatment efficacy.

The above objective and technical result are achieved by providing a device for conservative treatment of nose and paranasal sinuses diseases, comprising anterior and the posterior nose opening obturators, each of which is configured as an expandable shell made of elastic material and provided with a feed tube whose distal end is in communication with a cavity under the shell and whose proximal end is provided with an adapter having a valve mechanism, the posterior nose opening obturator shell being tightly fixed at the distal section of its feed tube, and the anterior nose opening obturator shell is tightly fixed onto the sleeve, the sleeve having two channels one of which houses the posterior nose opening obturator feed tube such that the sleeve is movable throughout the feed tube length, and the other channel houses a catheter used to evacuate pathological secretion from the paranasal sinuses and/or to administer pharmaceutical solutions into the paranasal sinuses for diagnostic or treatment purposes, the catheter is arranged in said channel such that its distal section is movable into the space between the shells of the obturators.

Furthermore, in the device for conservative treatment of nose and paranasal sinuses diseases the catheter may have at least one additional channel whose drainage port is located between the shells of the posterior and anterior nose openings' obturators, and the distal section of the catheter may be curved with respect to the catheter centerline. At least one additional round, oval, or rectangular shaped drainage port may be provided on the surface of the distal section of the catheter.

Furthermore, in the device for conservative treatment of nose and paranasal sinuses diseases, at least the distal section of the catheter and/or the posterior nose opening obturator feed tube may be reinforced with a flexible metal rod. In addition, the catheter of the proposed device more proximal of the sleeve may have a catheter limit stop while a sleeve retainer may be installed on the posterior nose opening obturator feed tube between the sleeve and the adapter with the valve mechanism. A sleeve position scale may be provided at the section along the feed tube of posterior nose opening obturator between the obturator's shell and the adapter with the valve mechanism.

Also, in the conservative treatment device of nose and paranasal sinuses diseases, at least one additional channel may be provided laterally to the feed tube channel with an inlet port being located on its proximal end and at least one drainage port may be positioned between the shells of the anterior and the posterior nose openings' obturators and may be round, oval or rectangular shaped.

The device for conservative treatment of nose and paranasal sinuses diseases may be furnished with an additional obturator configured as an expandable shell and a pressure channel, said shell being tightly secured to the posterior nose opening obturator feed tube between its shell and sleeve, and the additional obturator pressure channel is positioned laterally to the posterior nose opening obturator feed tube channel.

With the catheter being arranged in the respective sleeve channel such that it may move along the distal section between the obturators' shells, the drainage port of the catheter may be distanced away from nasal mucosal edema of the inferior turbinate and brought next to the area of the middle and superior nasal meatuses, i.e. directly to the area of the natural ostia of the paranasal sinuses. The extension of the distal section of the catheter to the middle and superior nasal meatuses ensures appropriate evacuation of pathological secretion from the paranasal sinuses and even distribution of a pharmaceutical solution in the sinuses which largely improves the procedure efficacy.

With the catheter being provided with at least one additional channel whose drainage port is located between the shells of the posterior and anterior nose openings' obturators, a pharmaceutical solution may be administered into the nasal cavity in parallel with the evacuation of exudate. A pharmaceutical solution washes over the intranasal structures and ensures the dilution of thick and viscous pathological secretions, thus facilitating their evacuation, while significantly improving the procedure efficacy.

With the catheter's distal portion being curved with respect to the centerline, the distal section may be elevated above the nasal mucosal edema of the inferior turbinate and bring it directly to the area of the middle and superior nasal meatuses, i.e. directly to the area of the natural ostia of the paranasal sinuses, which adds much more efficiency to the evacuation of pathological secretion and to the filling of the paranasal sinuses with a pharmaceutical solution.

Providing at least one additional drainage port on the surface of the distal section of the catheter, which may be round, oval or rectangular shaped, reduces the probability of the catheter being clogged with the nasal mucosal edema when intermittent pressure is produced in the nasal cavity and the paranasal sinuses followed by the evacuation of exudate which also makers treatment more efficacious.

Reinforcing at least one distal section of the catheter with a flexible metal rod improves the maneuverability of the catheter in the proposed device and improves the performance of the invention.

Providing a catheter limit stop on the catheter more proximal of the sleeve prevents the catheter from being pushed further up into the nasal cavity and/or catheter's drainage port being inserted into the sleeve.

Reinforcing the posterior nose opening obturator feed tube with a flexible metal rod improves the maneuverability of the proposed device's tube and improves the performance of the device.

By positioning the posterior nose opening obturator feed tube between the sleeve and the adapter with the retainer's valve mechanism, the device is secured in the area of the columella and the ala of the nose when the shell of the posterior nose opening obturator expands, whereas the physician is not required to hold the device in the hand. Furthermore, the retainer secures the position of the sleeve in the nasal vestibule during a treatment procedure thus ensuring that the nasal cavity remains airtight.

By providing the sleeve position scale in the area of the posterior nose opening obturator feed tube between its shell and the adapter with the valve mechanism, the optimum distance between the obturators shells may be determined during the first treatment procedure and the sleeve may be set at the same distance during follow-up treatment procedures which also delivers a better performance of the device.

By providing laterally to the feed tube's channel at least one additional channel with an inlet port at its proximal end and with at least one drainage port which is located between the shells of the posterior and anterior nose opening obturators and may be round, oval or rectangular shaped, a pharmaceutical solution may be administered into the nasal cavity in parallel with the evacuation of exudate. Administered via the additional channel, a pharmaceutical solution washes over the intranasal structures and ensures the dilution of thick and viscous pathological secretions, thus facilitating their evacuation via the catheter, while significantly improving the procedure efficacy.

By providing the device with an additional obturator configured as an expandable shell and a pressure channel, said shell is tightly secured to the posterior nose opening obturator feed tube between its shell and sleeve, while the pressure channel positioned laterally to the posterior nose opening obturator feed tube channel enables the device to be used to staunch nasal bleeding that may start during a treatment procedure thus adding more functionality to the proposed device.

The drawings show the proposed conservative treatment device for nose diseases, where FIG. 1 shows the proposed device for conservative treatment of nose and paranasal sinuses diseases in its operating state, i.e. when it is inserted into a nasal cavity to the operational position to perform a treatment procedure;

FIG. 13 illustrates the proposed device provided with an additional obturator

Figure 1:
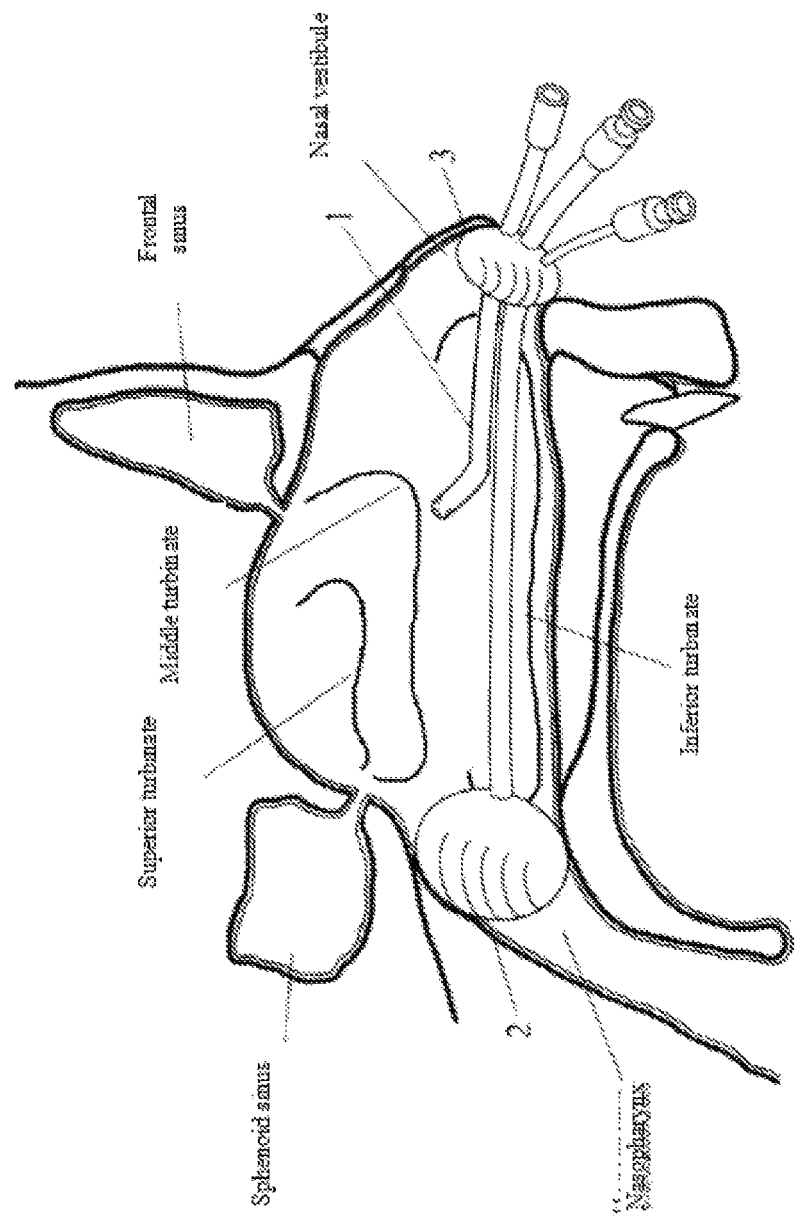

A device for conservative treatment of nose and paranasal sinuses diseases comprises a catheter 1 through which intermittent (negative and positive) pressure is produced in an isolated nasal cavity followed by subsequent evacuation of pathological secretion from the paranasal sinuses and/or filling them with a pharmaceutical solution for diagnostic or treatment purposes (FIG. 1). The device also comprises an obturator 2 of the posterior nose opening (hereinafter the posterior obturator) and obturator 3 of anterior nose opening (hereinafter the anterior obturator) that, when used collectively, isolate the nasal cavity on the side of the nasopharynx and the nasal vestibule.

Figure 2:
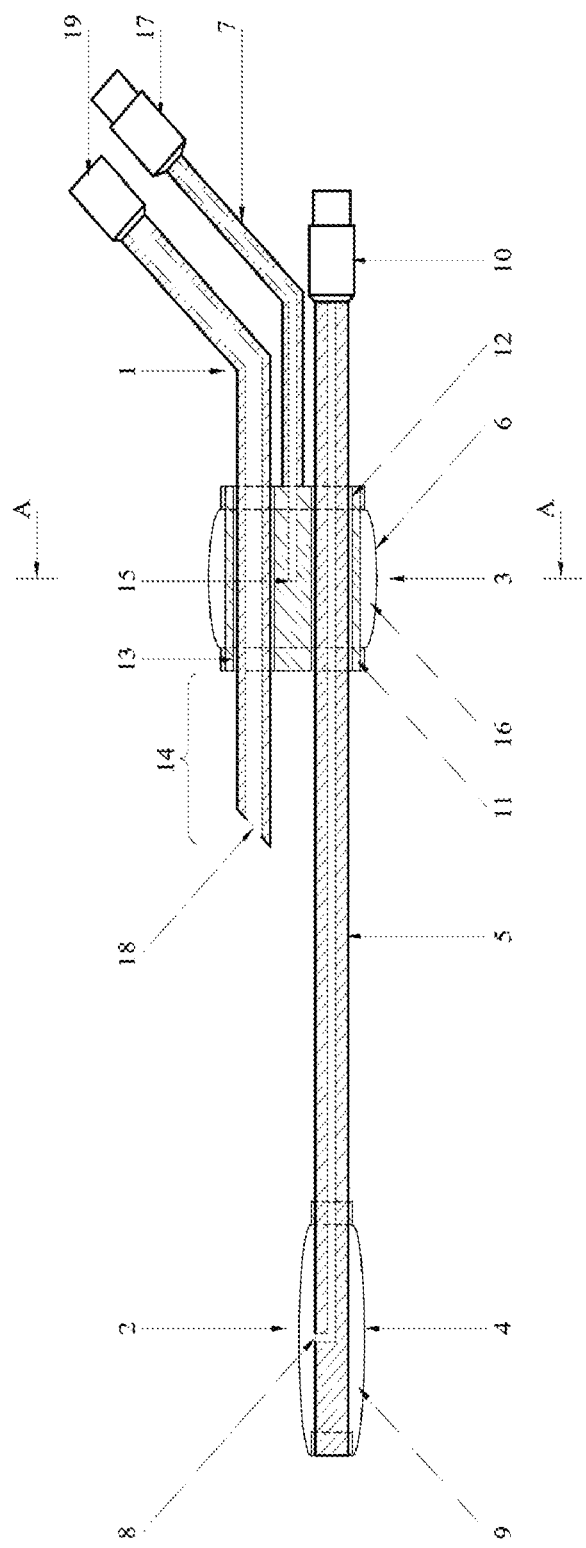
FIG. 2 shows the design of the device for conservative treatment of nose and paranasal sinuses diseases.

The posterior obturator 2 is comprised of an expandable shell 4 and a feed tube 5 (FIG. 2). The anterior obturator 3 is comprised of an expandable shell 6 and a feed tube 7. Any polymer with elastic properties, such as latex, may be used in the manufacture of the shells. However, the obturator shells should be preferably made of silicone rubber which has a higher elasticity as compared to latex requiring lower internal pressure to be produced to cause the silicone rubber obturator shell to expand. Therefore, when the shell expands in the nasal cavity, the pressure applied to on tissues from the shell will be minimized.

Shell 4 of posterior obturator 2 is tightly secured at the distal end of feed tube 5 so that its drainage port 8 is housed in interior space 9 of shell 4 in a way to allow interior space 9 of shell 4 to be connected to the positive pressure source, e.g., a syringe (not shown), via feed tube 5. A gas (e.g., air) or a liquid (e.g., water) pressure applied into interior space 9 via feed tube 5 from the positive pressure source causes shell 4 to expand radially outward reaching its operating state as shown in FIG. 1. To provide a connection to the positive pressure source, the proximal end of feed tube 5 is provided with adapter 10 having a valve mechanism (FIG. 2), thus preventing reverse flow of the gas or liquid from interior space 9 of shell 4 and maintaining desired pressure within it.

Provision is made in the proposed device for measuring the distance between shells 4 and 6 of the obturators to ensure full isolation on the side of the nasopharynx and the nasal vestibule in individuals having different nose lengths which is achieved by the structural design (FIG. 2). The section of feed tube 5 between shell 4 and adapter 10 having valve mechanism is furnished with sleeve 11 with two channels 12 and 13 (FIG. 2) provided in it. Channel 12 houses feed tube 5 of posterior obturator 2 so that sleeve 11 is movable along the entire length of feed tube 5. Channel 13 is provided with catheter 1 in such a way that its distal section 14 is movable between shells 4 and 6 of the obturators, i.e. into the isolated portion of the nasal cavity.

Figure 3:
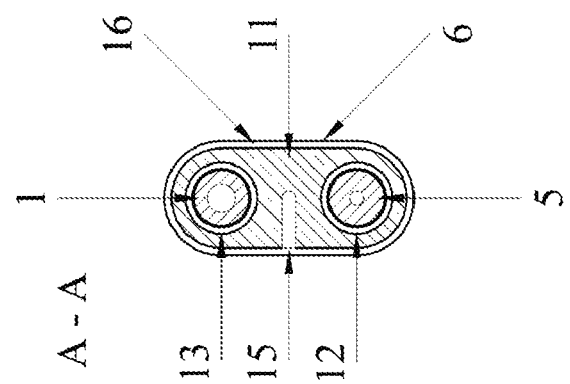
FIG. 3 shows the cross-section along the A-A line in FIG. 2.

Shell 6 of the anterior obturator 3 is tightly fixed onto sleeve 11, while the distal end of feed tube 7 is secured onto sleeve 11 in a manner that allows drainage port 15 of feed tube 7 to be connected to interior space 16 of shell 6 (FIG. 3). As such, interior space 16 of shell 6 is connected to the positive pressure source, e.g., a syringe (not shown), via feed tube 7. A gas (e.g. air) or a liquid (e.g. water) pressure applied to interior space 16 via feed tube 7 from the positive pressure source causes shell 6 to expand radially outward reaching its operating state as shown in FIG. 1. To provide a connection to the positive pressure source, the proximal end of feed tube 7 is provided with adapter 17 having a valve mechanism (FIG. 2), thus preventing reverse flow of the gas or liquid from interior space 16 of shell 6 and maintaining desired pressure within it.

The movement of sleeve 11 relative to feed tube 5 makes it possible to select the optimum distance between shell 4 of the posterior obturator 2 and shell 6 of the anterior obturator 3 for a specific patient allowing for the length of a patient's nose.

While the device remains in the conveying mode, shell 4 tightly fits against feed tube 5 and shell 6—against the surface of sleeve 11 creating no obstruction to the device's movements within the nasal cavity.

In the proposed device for conservative treatment of nose and paranasal sinuses diseases, catheter 1 is movably arranged in channel 13 of sleeve 11, thus enabling distal section 14 of catheter 1 to be extended into the space between shells 4 and 6 of the obturators, i.e. into an isolated portion of the nasal cavity. So drainage port 18 of catheter 1 is distanced away from the nasal mucosal edema of the inferior turbinate and brought next to the area of the middle and superior nasal meatuses, i.e. directly to the area of the natural ostia of the paranasal sinuses. The proximal end of catheter 1 is furnished with adapter 19 for connection to a syringe or an aspirator.

Figure 4:
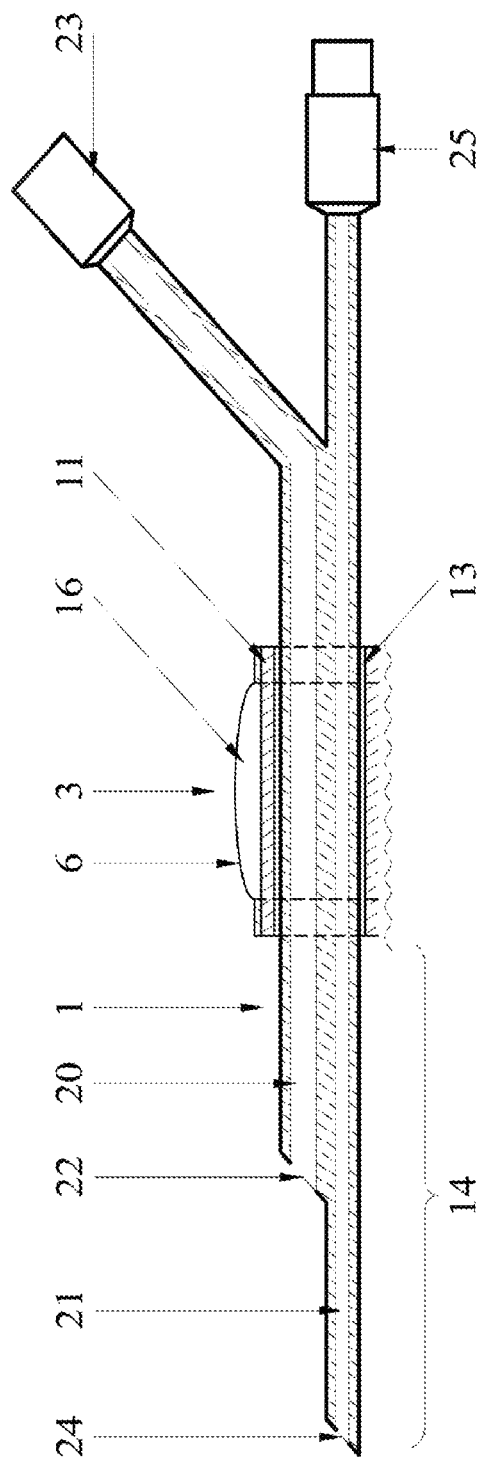
FIG. 4 illustrates the proposed device provided with a catheter having an additional channel.

In the proposed device, catheter 1 may include, in addition to main channel 20, at least one additional channel 21 (FIG. 4). Main channel 20 is provided with drainage port 22 and configured to produce intermittent pressure in the nasal cavity and the paranasal sinuses followed by the evacuation of exudate. To provide a connection to a syringe or an aspirator, the proximal end of main channel 20 is furnished with adapter 23. Additional channel 21 is provided with drainage port 24 and configure to administer a pharmaceutical solution (e.g., an antiseptic solution) into the nasal cavity. To provide a connection to a syringe, the proximal end of additional channel 21 is furnished with adapter 25 having a valve mechanism, thus preventing reverse flow of the pharmaceutical solution out of the nasal cavity and blocking the passage of air into the nasal cavity when intermittent pressure is produced and pathological secretion is evacuated.

Figure 5:
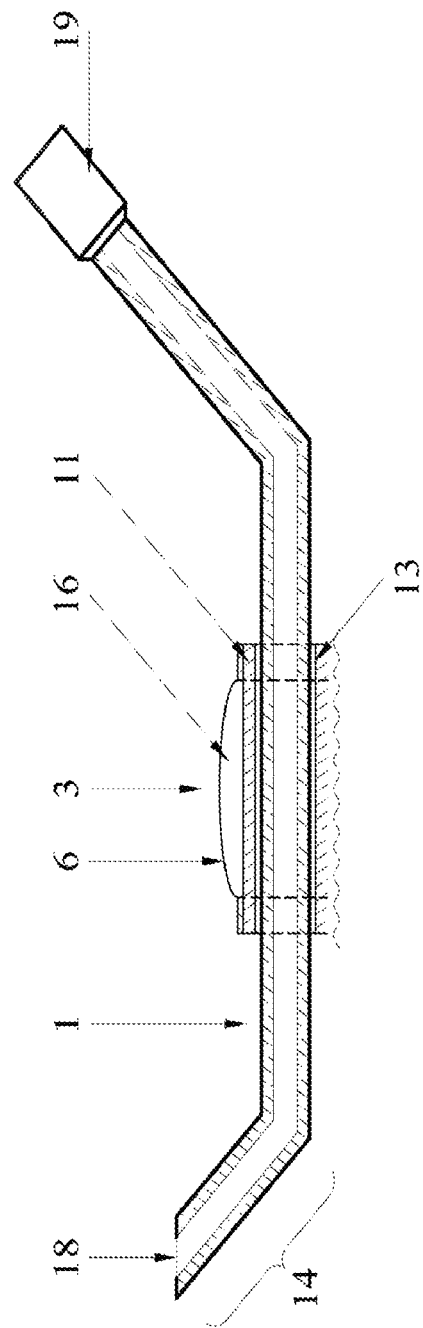
FIG. 5 illustrates the proposed device with a catheter curved with respect to the centerline of the distal section.

Distal section 14 of catheter 1 may be curved with respect to the centerline (FIG. 5).

Figure 6:
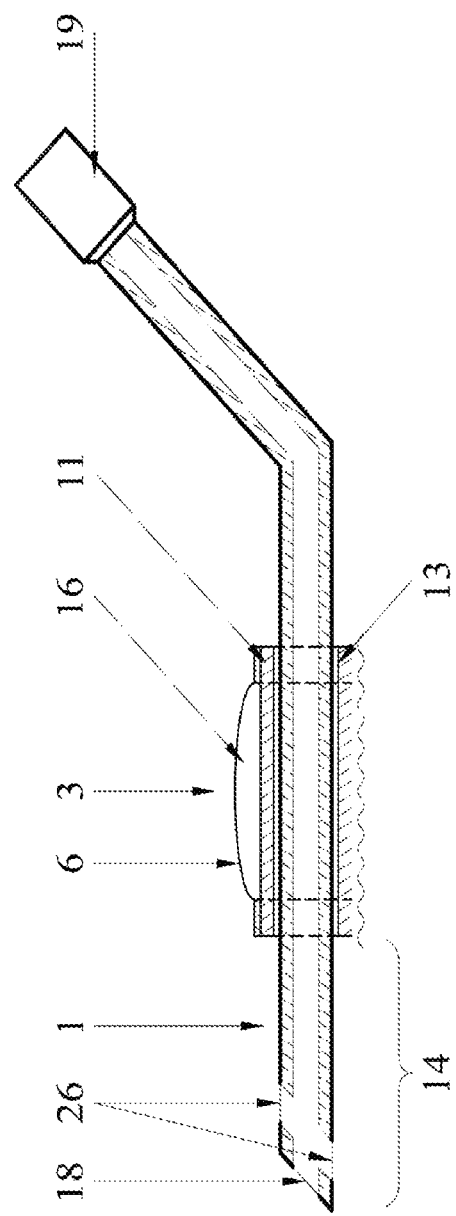
FIG. 6 illustrates the proposed device with a catheter with additional drainage ports along the distal section.

In the proposed device structure, the surface of distal section 14 of catheter 1 can have one additional drainage port 26 round, oval or rectangular shaped (FIG. 6).

Figure 7:
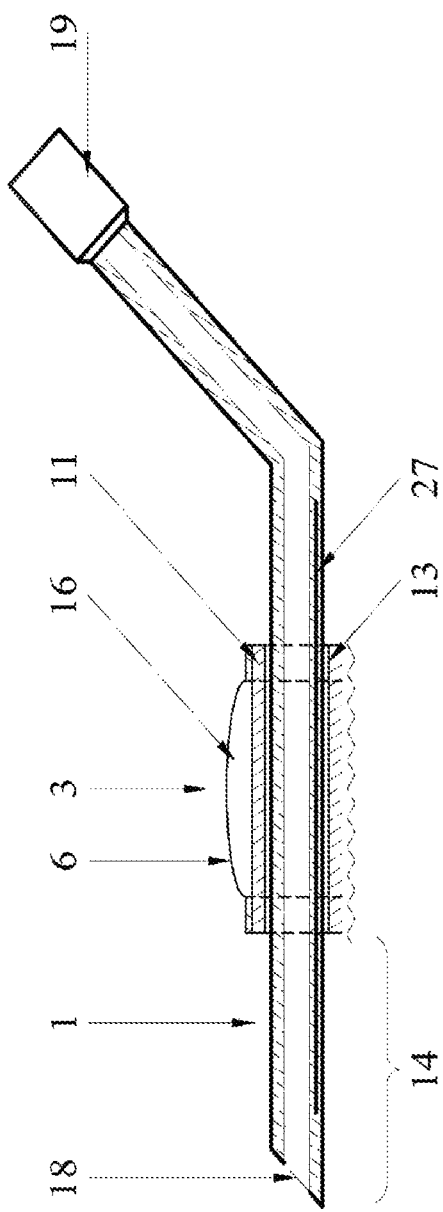
FIG. 7 illustrates the proposed device provided with a catheter reinforced by a flexible metal rod.

To improve the maneuverability of catheter 1 in the proposed device, it may be reinforced with a flexible metal rod 27 (FIG. 7), at least in the area of distal section 14.

Figure 8:
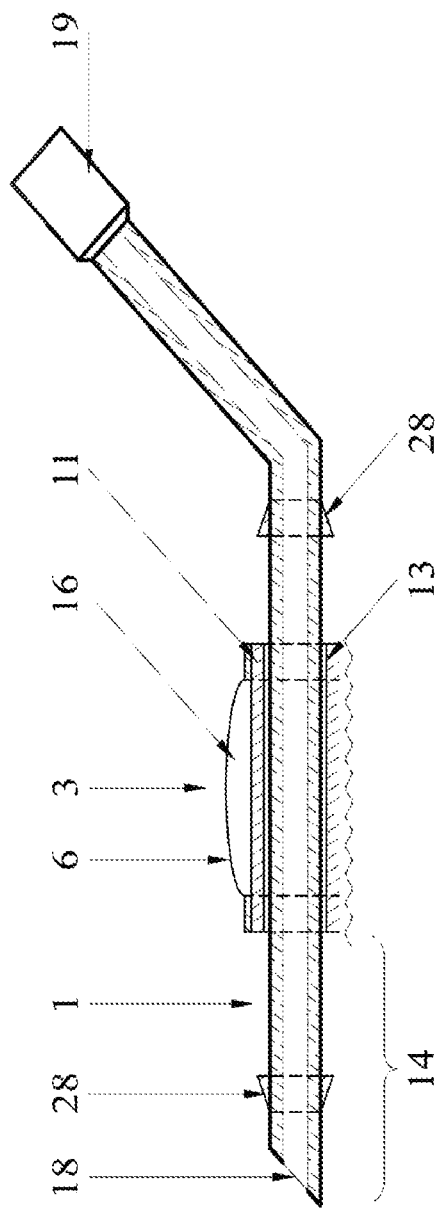
FIG. 8 illustrates the proposed device provided with a catheter having limit stops.

Catheter 1 may be configured with limit stop 28 (e.g., as a conical protrusion) (FIG. 8). Limit stop 28 may be provided more proximal of sleeve 11 (preventing distal section 14 of catheter 1 from being pushed further up into the nasal cavity), more distal of sleeve 11 (preventing the drainage port of catheter 18 from being inserted into sleeve 11) and more proximal and more distal of sleeve 11 (allowing for a pre-set slack of catheter 1).

Figure 9:
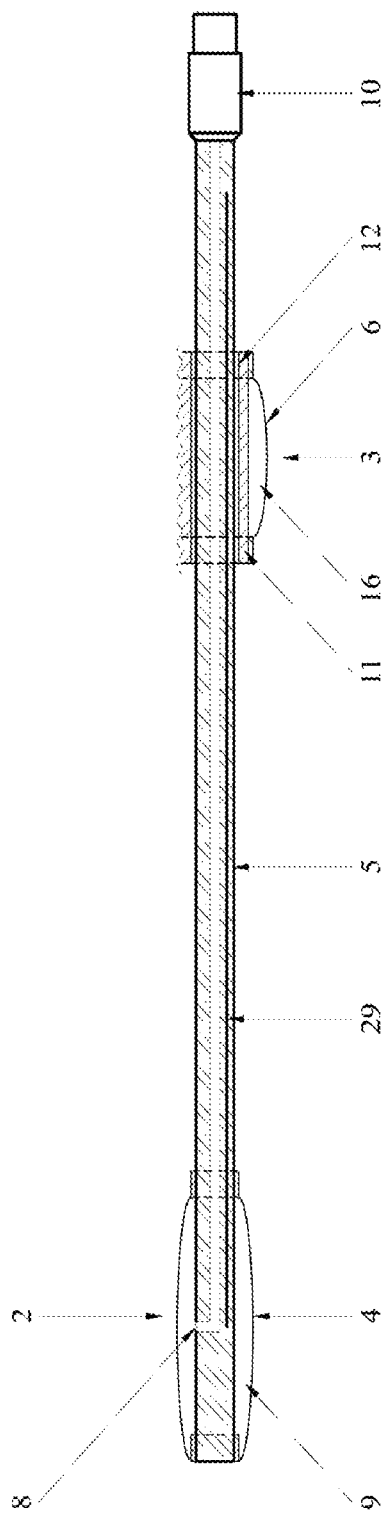
FIG. 9 shows the proposed device provided with a the posterior nose opening obturator feed tube reinforced with a flexible metal rod.

To improve the maneuverability of the proposed device and, therefore, its operational properties, feed tube 5 of the posterior obturator 2 may be reinforced with flexible metal rod 29 (FIG. 9).

Figure 10:
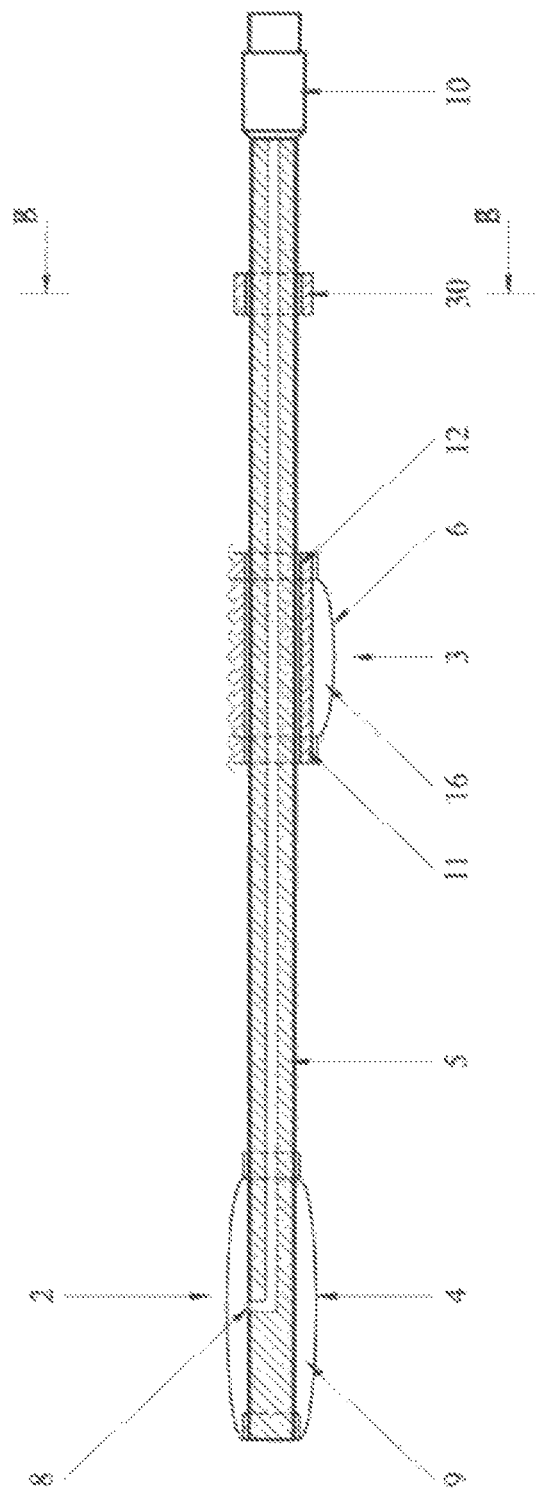
FIG. 10 shows the proposed device furnished with a sleeve retainer.
Figure 11:
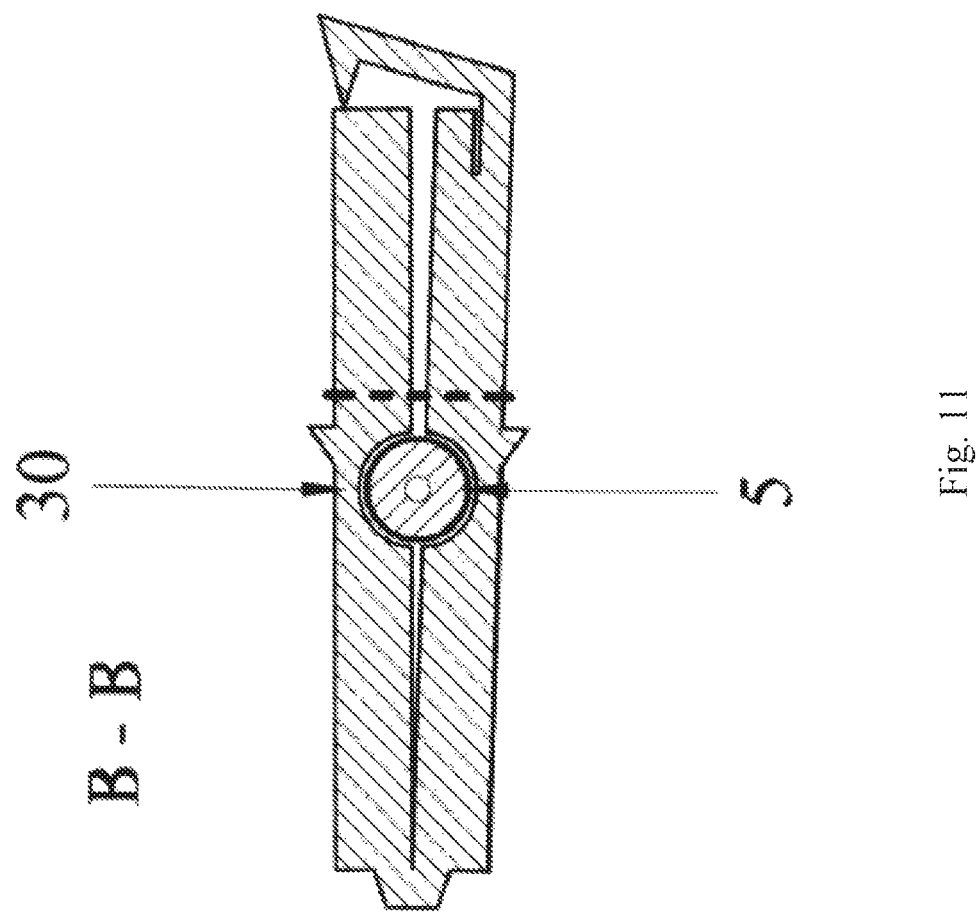
FIG. 11 shows the cross-section along the B-B line in FIG. 10.

For the better performance of the proposed device, to prevent shell 4 of the posterior obturator 2 from slipping out of the nasopharynx into the oropharynx and sleeve 11 together with shell 6 of the anterior obturator 3 from sliding away, provision is made for retainer 30 (e.g. in the form of a clip) (FIG. 10, 11) that is installed on the section of feed tube 5 in the posterior obturator 2 between sleeve 11 and adapter 10 having the valve mechanism. In the conveying mode retainer 30 can move over feed tube 5. Once the optimum distance between shells 4 and 6 of the obturators are selected, retainer 30 is brought close to sleeve 11 and into operation so that it gets fixed relative to feed tube 5 and sets a stop for the device in the area of the columella and the ala of the nose.

Also the performance is improved by providing feed tube 5 of the posterior obturator 2 between its shell 4 and adapter 10 having valve mechanism with the sleeve position scale (not shown).

Figure 12:
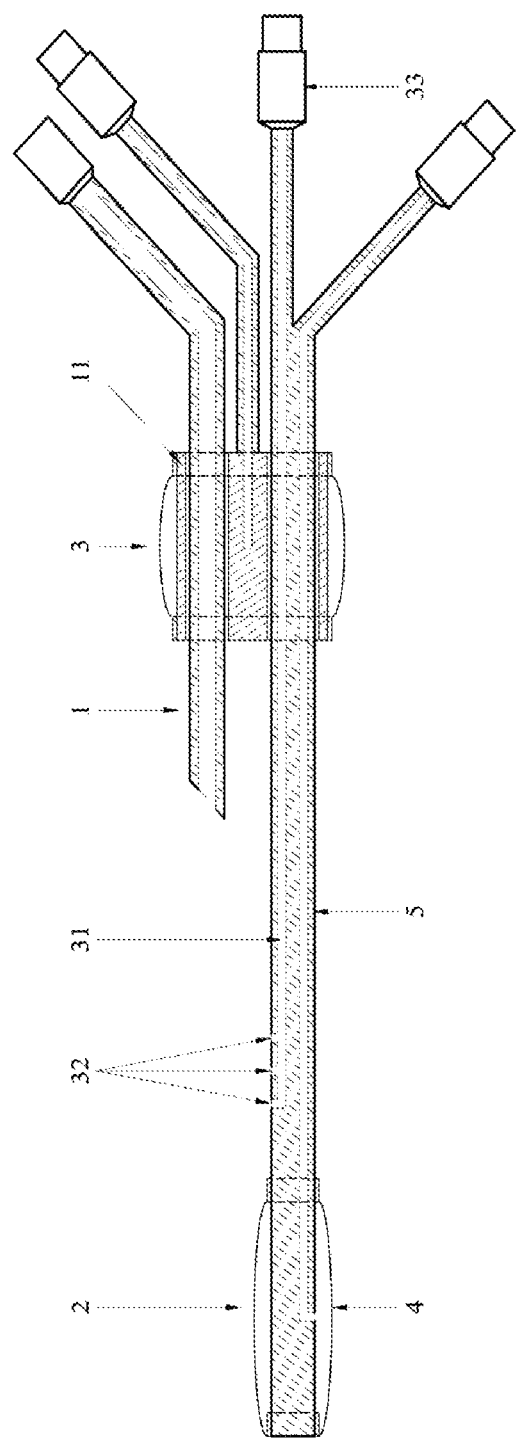
FIG. 12 illustrates the proposed device provided with an additional channel in the posterior nose opening obturator feed tube.

The proposed device for the conservative treatment of nose and paranasal sinuses diseases may contain at least one additional channel 31 that is positioned laterally to the channel of feed tube 5. It should be noted that it does not matter how additional channel 31 will be configured: whether as part of feed tube 5 (FIG. 12) or as a separate component, i.e. a tube arranged along feed tube 5. Herein, at least one drainage port 32 in additional channel 31 is provided between shells 4 and 6 of the posterior and the anterior obturators, the drainage port 32 may be round, oval or rectangular shaped. A pharmaceutical solution (e.g., an antiseptic solution) is administered into the nasal cavity via additional channel 31 and it is removed via catheter 1 by a syringe and an aspirator. To provide a connection to a syringe, the proximal end of additional channel 31 is furnished with adapter 33 having the valve mechanism, thus preventing reverse flow of the pharmaceutical solution out of the nasal cavity and blocking the passage of air into nasal cavity when intermittent pressure is produced and pathological secretion is evacuated.

Nasal bleeding out of the blood vessels providing blood supply to the nasal mucosa may be caused by intermittent pressure produced to evacuate pathological secretion during a treatment procedure. As a result, blood starts to run through catheter 1. To stanch such bleeding, the device may be provided with additional obturator 34 (FIG. 13). Additional obturator 34 is configured as expandable shell 35 tightly connected to feed tube 5 of the posterior obturator 2 and pressure channel 36. Shell 35 is arranged in the section of feed tube 5 of the posterior obturator 2 between its shell 4 and sleeve 11, while pressure channel 36 of additional obturator 34 is positioned laterally to feed tube 5 channel. Drainage port 37 of pressure channel 36 is in communication with interior space 38 of shell 35. As such, interior space 38 of shell 35 is connected to the positive pressure source, e.g. a syringe (not shown), via pressure channel 36. A gas (e.g. air) or a liquid (e.g. water) pressure applied to interior space 38 via pressure channel 36 from the positive pressure source causes shell 35 to expand radially outward reaching its operating state. To provide a connection to the positive pressure source, the proximal end of pressure channel 36 is furnished with adapter 39 having the valve mechanism, thus preventing reverse flow of the gas or liquid from interior space 38 of shell 35 and maintaining desired pressure in it.

While the device remains in the conveying mode, shell 35 tightly fits against feed tube 5 creating no obstruction to the device's movements within the nasal cavity.

The proposed device operates in the following manner.

The device for conservative treatment of nose and paranasal sinuses diseases is shaped to match the anatomy of the nasal cavity. To that end, the distance from the nasal vestibule to the nasopharynx is measured and set between shells 4 and 6 of the obturators according to the measurement.

The position of sleeve 11 is fixed by a J-type curve of feed tube 5 of the posterior obturator 2 more proximal of sleeve 11 (in the same way as in the prior art device) and, where the embodiment of the proposed device with retainer 30 (e.g. in the form of a clip) is used, said clip is brought next to sleeve 11 in its operating state in such a way as to set retainer 30 rigidly in place against feed tube 5 and to provide a stop in the area of the columella and the ala of the nose.

To save the time for follow-on procedures, the embodiment of the device with visual indication of sleeve 11 position (the sleeve position scale provided at the section of feed tube 5 of the posterior obturator between its shell 4 and the adapter 10 having the valve mechanism) may be used. Having selected the optimum distance between shells 4 and 6 of the obturators during the first treatment procedure, the physician enters data on the position of sleeve 11 into the patient's chart with reference to the scale and places sleeve 11 on the same spot for follow-on treatment procedures.

Then the distance from the nasal vestibule to the middle turbinate is measured. Referring to the obtained measurement while moving catheter 1 along sleeve 11, its distal section 14 is extended so that drainage port 18 of catheter 1 could be brought as close as possible to the area of the middle and superior nasal meatuses.

The device is inserted under direct vision into the nasal cavity along the lower line of the common nasal meatus parallel to the inferior turbinate as further up as the nasopharynx.

The anterior obturator 3 is set in the nasal vestibule and, under visual control, distal section 14 of catheter 1 is brought close to the area of the middle and superior nasal meatuses.

Subsequent to that, shell 4 of the posterior obturator 2 is expanded in the nasopharynx. 10-12 ml of gas 4 (e.g. air) or liquid (e.g. water) is administered into interior space 9 under shell using a syringe via adapter 10 having the valve mechanism. Dosed injection of gas or liquid under the shell causes shell 4 to expand in a controlled manner and isolate the nasal cavity on the side of the nasopharynx.

Subsequent to that, shell 6 of the anterior obturator 3 is expanded in the nasal vestibule. 6-8 ml of gas 6 (e.g. air) or liquid (e.g. water) is administered into interior space 16 of shell 6 using a syringe via adapter 17 having the valve mechanism. Dosed injection of gas or liquid under the shell causes shell 6 to expand in a controlled manner and isolate the nasal cavity on the side of the nasal vestibule.

By doing the above, the nasal cavity and paranasal sinuses are isolated from the ambience on the side of the nasal vestibule and nasopharynx.

After that, a 20 ml syringe is connected to catheter 1 via adapter 19, with the syringe plunger set at the 10 ml mark. By moving the syringe plunger up and down, negative and positive pressure is produced in the nasal cavity and paranasal sinuses. The plunger is moved inside the syringe body from the 14 ml mark to 6 the ml mark, which has been found to produce pressure equivalent to +/−10-15 mbar in the nasal cavity.

In response to intermittent pressure so produced, exudate makes way from the paranasal sinuses into the nasal cavity and then into the syringe. The evacuation of pathological secretion goes on until it stops getting into the syringe. Once evacuation is complete, the syringe is disconnected from catheter 1.

Subsequent to that, a syringe containing a pharmaceutical solution is connected to catheter 1 via adapter 19. The first portion of the solution containing a maximum of 1 ml is administered into the nasal cavity followed by the return of the plunger to its original position evacuating air from the paranasal sinuses. At the same time, negative pressure builds up in the sinuses and the solution flows into them. The sequential administration of the drug and the building of negative pressure results in the paranasal sinuses being filled up with the pharmaceutical solution. Once the pharmaceutical solution is administered, the syringe is disconnected from catheter 1.

After the pharmaceutical solution has been administered into the paranasal sinuses, gas or liquid is removed from under shell 6 of the anterior obturator 3 and then from under shell 4 of the posterior obturator 2. The device is extracted from the nasal cavity.

Where the proposed device for conservative treatment of nose and paranasal sinuses diseases has a catheter provided with at least one additional channel 21, such device may be used to simultaneously evacuate pathological secretions and irrigate the nasal cavity with a pharmaceutical solution (e.g. an antiseptic solution).

At the same time, posterior obturator 2 and the anterior obturator 3, sleeve 11 and the other structural elements are inserted in the manner similar to described above for the device without an additional channel of catheter 1 configured such as to enable the axial movement of catheter 1.

Alterations in the workings of the device with an additional channel apply only to the operation of main channel 20 and additional channel 21 of catheter 1.

A syringe or an aspirator is connected to main channel 20 of catheter 1 via adapter 23. A syringe containing a pharmaceutical solution is connected to additional channel 21 of catheter 1 via adapter 25 having the valve mechanism.

Intermittent pressure is produced in the nasal cavity via main channel 20 of catheter 1 for 1-2 minutes to move pathological secretions from the paranasal sinuses into the nasal cavity. If exudate has a thick and viscous consistency, a pharmaceutical solution is jet injected into the nasal cavity via additional channel 21. The pharmaceutical solution enters into the nasal cavity via drainage port 24 of additional channel 21 and washes over the nasal mucosa of the nasal cavity in the isolated space between shells 4 and 6 of the obturators and exits via main channel 20 of catheter 1 into a syringe or an aspirator's receptacle. The evacuation of exudate out of the nasal cavity is largely intensified due to its dilution. The procedure is carried out until wash water contains pathological secretion.

Once the procedure is complete, the gas or liquid is removed from under shell 6 of the anterior obturator 3 and then from under shell 4 of the posterior obturator 2. The device is extracted from the nasal cavity.

The proposed device equipped with additional channel 31 works in a similar way.

If the proposed device for conservative treatment of nose and paranasal sinuses diseases has additional obturator 34, such device may be used to evacuate pathological secretions from the paranasal sinuses and subsequently to administer a pharmaceutical solution into the paranasal sinuses (with only one channel of the catheter in operation), to simultaneously evacuate pathological secretions and irrigate the nasal cavity with a pharmaceutical solution (with the main and additional channels of the catheter/the catheter's channels or the catheter's channel and the additional channel/the channels of the posterior obturator feed tube in operation) and also to staunch bleeding that is started during a treatment procedure.

At the same time, posterior obturator 2 and the anterior obturator 3, sleeve 11 and the other structural elements are inserted in the manner similar to described above for the device without an additional channel of catheter 1 configured such as to enable the axial movement of catheter 1. Also shell 35 of additional obturator 34 tightly fits against the surface of feed tube 5. Once the nasal cavity is isolated on the side of the nasopharynx and nasal vestibule, a treatment procedure is commenced as described above for devices with a single-catheter channel or for devices with the main and additional channels/the catheter's channels or for devices with the catheter's channel and the additional channel/channels of the feed tube in the posterior obturator.

Should blood get into a syringe via catheter 1, the evacuation of exudate stops and shell 35 of additional obturator 34 is expanded in the nasal cavity. For this purpose a gas (e.g. air) or a liquid (e.g. water) is administered by a syringe via adapter 39 having the valve mechanism into interior space 38 of shell 35 via pressure channel 36 in quantities required to provide compression in the bleeding area of the nasal mucosa in the nasal cavity.

Once the hemostatic effect is achieved, the gas or liquid is removed from under shell 6 of the anterior obturator 3, then from under shell 35 of additional obturator 34 and finally from under shell 4 of the posterior obturator 2. The device is extracted from the nasal cavity.

Therefore, as compared to the prior art device, the claimed device for the conservative treatment of nose and paranasal sinuses diseases has an improved performance and functionality, provides more efficacious and reliable treatment of sinusitis and has an expanded scope of application.

The invention claimed is:

1. A device for conservative treatment of nose and paranasal sinuses diseases, comprising anterior and the posterior nose opening obturators, each obturator comprises an expandable shell made of elastic material and provided with a first feed tube and a second feed tube, a distal end of the first feed tube is in communication with a cavity under the shell of the posterior obturator and a distal end of the second feed tube is in communication with a cavity under the shell of the anterior obturator; a proximal end of the first feed tube is provided with an adapter having a valve mechanism, and a proximal end of the second feed tube is provided with an adapter having a valve mechanism, the posterior nose opening obturator shell being tightly fixed at the distal section of the feed tube of the posterior nose opening obturator, feed tube, and the anterior nose opening obturator shell is tightly fixed onto the sleeve, wherein the sleeve have two channels one of which houses the posterior nose opening obturator feed tube such that the sleeve can be moved along the entire length of the feed tube, and the other channel houses a catheter used to evacuate pathological secretion from the paranasal sinuses or to administer pharmaceutical solutions into the paranasal sinuses for diagnostic or treatment purposes, wherein the catheter is arranged in said channel such that distal section of the catheter is movable into the space between the shells of the obturators and wherein a catheter movement limiter is provided on the distal section of the catheter.

2. The device for conservative treatment of nose and paranasal sinuses diseases of claim 1, wherein the catheter is furnished with at least one additional channel having drainage port is located between the shells of the posterior and anterior nose openings' obturators.

3. The device for conservative treatment of nose and paranasal sinuses diseases of claim 1, wherein the distal section of the catheter is curved with respect to a centerline.

4. The device for conservative treatment of nose and paranasal sinuses diseases of claim 1, wherein at least one additional drainage port is provided on the surface of the distal section of the catheter.

5. The device for conservative treatment of nose and paranasal sinuses diseases of claim 4, wherein the drainage port is selected from the group consisting of round, oval or rectangular shaped.

6. The device for conservative treatment of nose and paranasal sinuses diseases of claim 1, wherein at least one distal section of the catheter is reinforced with a flexible metal rod.

7. The device for conservative treatment of nose and paranasal sinuses diseases of claim 1, wherein the posterior nose opening obturator feed tube is reinforced with a flexible metal rod.

8. The in that wherein a retainer is arranged on the posterior nose opening obturator feed tube between the sleeve and the adapter having the valve mechanism.

9. The device for conservative treatment of nose and paranasal sinuses diseases of claim 1, wherein a sleeve position scale is provided at a section of the posterior nose opening obturator feed tube between its shell and adapter having the valve mechanism.

10. The device for conservative treatment of nose and paranasal sinuses diseases of claim 1, that wherein at least one additional channel is provided laterally to the feed tube's channel, while an inlet port of the additional channel is located at a proximal end, and at least one drainage port located between the shells of the posterior and anterior nose opening obturators.

11. The device for conservative treatment of nose and paranasal sinuses diseases of claim 10, wherein the drainage port of the additional channel is selected from the group consisting of round, oval or rectangular shaped.

12. The device for conservative treatment of nose and paranasal sinuses diseases of claim 1, wherein it is furnished with an additional obturator configured as an expandable shell and a pressure channel, said shell being tightly secured to the posterior nose opening obturator feed tube between the shell and sleeve, and the additional obturator pressure channel is positioned laterally to the posterior nose opening obturator feed tube channel.

13. A device for conservative treatment of nose and paranasal sinuses diseases, comprising anterior and the posterior nose opening obturators, each obturator comprises an expandable shell made of elastic material and provided with a first feed tube and a second feed tube, a distal end of the first feed tube is in communication with a cavity under the shell of the posterior obturator and a distal end of the second feed tube is in communication with a cavity under the shell of the anterior obturator; a proximal end of the first feed tube is provided with an adapter having a valve mechanism, and a proximal end of the second feed tube is provided with an adapter having a valve mechanism, the posterior nose opening obturator shell being tightly fixed at the distal section of its feed tube, and the anterior nose opening obturator shell is tightly fixed onto the sleeve, wherein the sleeve have two channels one of which houses the posterior nose opening obturator feed tube such that the sleeve can be moved along the entire length of the feed tube, and the other channel houses a catheter used to evacuate pathological secretion from the paranasal sinuses or to administer pharmaceutical solutions into the paranasal sinuses for diagnostic or treatment purposes, wherein the catheter is arranged in said channel such that distal section of the catheter is movable into the space between the shells of the obturators and wherein a catheter movement limiter is provided on the more proximal section of the catheter.

* * * * *